（12）United States Patent
Wang et al.

(10) Patent No.: US 9,061,236 B2
(45) Date of Patent: Jun. 23, 2015

(54) GEL ELECTROPHORESIS DEVICE FOR LOADING LARGE SAMPLE VOLUMES

(71) Applicant: Nanjingjinsirui Science & Technology Biology Corporation, Nanjing (CN)

(72) Inventors: Zhuying Wang, Monmouth Junction, NJ (US); Hong Qian, Nanjing (CN); Yuanming Liao, Nanjing (CN); Tao Bai, Nanjing (CN)

(73) Assignee: Nanjingjinsirui Science & Technology Biology Corporation, Nanjing (CN)

( * ) Notice: Subject to any disclaimer, the term of this patent is extended or adjusted under 35 U.S.C. 154(b) by 238 days.

(21) Appl. No.: 13/682,125

(22) Filed: Nov. 20, 2012

(65) Prior Publication Data

US 2014/0138249 A1    May 22, 2014

(51) Int. Cl.
*G01N 27/453* (2006.01)
*B01D 57/02* (2006.01)
*G01N 27/447* (2006.01)

(52) U.S. Cl.
CPC .......... *B01D 57/02* (2013.01); *G01N 27/44743* (2013.01); *G01N 27/44782* (2013.01); *G01N 27/453* (2013.01)

(58) Field of Classification Search
CPC ........... G01B 27/447; G01B 27/44704; G01B 27/44743
USPC ................................................. 204/606–620
See application file for complete search history.

(56) References Cited

U.S. PATENT DOCUMENTS 5,411,657 A    5/1995  Leka

FOREIGN PATENT DOCUMENTS

EP    0735365 A2    10/1996

OTHER PUBLICATIONS

Int'l Search Report and Written Opinion Issued Feb. 4, 2014 in Int'l Application No. PCT/US2013/070263.
Applied Biosystems: "ABI Prism 377 DNA Sequencer 96-Lane Upgrade User's Manual," retrieved from the internet at: http://tools.lifetechnologies.com/content/sfs/manuals/cms_041005.pdf (Jan. 1, 2000).
Biocom, "Vertical Gel Units," retrieved from the internet at: http://www.biocomdirect.com/pdfs/Biocom_Catalogue_EP_Vert.pdf (Apr. 4, 2002).

*Primary Examiner* — J. Christopher Ball
(74) *Attorney, Agent, or Firm* — Panitch Schwarze Belisario & Nadel LLP

(57) ABSTRACT

A device for gel electrophoresis is provided having larger wells for loading an increased sample volume with improved gel resolution. The device includes a gel cassette having a front plate and a back plate, wherein at least one plate has a stepped inner surface to create a wider opening at the top of the gel cassette, a gel matrix, and a comb with teeth having a thickness substantially equal to the spacing at the top opening of the gel cassette. Using this device, the sample volume in each well can be increased and the sample height in each well can be significantly reduced, as compared to loading the same volume in the wells of a standard gel cassette.

14 Claims, 12 Drawing Sheets

GEL ELECTROPHORESIS DEVICE FOR LOADING LARGE SAMPLE VOLUMES

FIELD OF THE INVENTION

The present invention relates to a device for performing gel electrophoresis. In particular, the invention relates to an improved gel electrophoresis device for the separation of biological macromolecules that allows for loading an increased sample volume with improved gel resolution.

BACKGROUND OF THE INVENTION

Gel electrophoresis is a commonly used technique for the separation of biological molecules such as proteins and nucleic acids (DNA and RNA). Generally, the method involves applying an electric current to a porous, polymerized gel matrix that contains the biological mixture. The components of the mixture will migrate through the gel matrix at different rates, most often dependent on charge and/or size. Movement of the molecules through the polymerized gel matrix produces a series of bands, with each band corresponding to a different molecule.

Acrylamide or agarose gel matrices are typically used for the separation of the biological molecules. The gel matrix is formed by copolymerization with crosslinking reagents which creates a pore structure that allows for the passage of molecules through the gel matrix. Other gels, such as starch gels, have also been used for electrophoresis. Selection of the gel matrix material most often depends on the type of biological molecules to be separated. For protein separation, polyacrylamide gel electrophoresis (PAGE) is popular because polyacrylamide gels are optically transparent, and the pore sizes are in a range that is suitable for proteins. Proteins with different charge/mass ratios will move through the polyacrylamide matrix at different rates. Using a series of known molecular weight proteins as a marker, the size and/or the molecular weight of the specific protein of interest can be estimated.

Polyacrylamide gels were first used as a supporting matrix for gel electrophoresis in 1959 by Raymond and Weintraub (Raymond, S. and Weintraub, L. Acrylamide gel as a supporting medium for zone electrophoresis. *Science*, 1959, 130: 711-711) and were well studied by Ornstein (Ornstein, L. Disc Electrophoresis, 1, Background and Theory. *Ann. New York Acad. Sci.*, 1964, 121: 321-349) and Davis (Davis, B. J. Disc Electrophoresis. 2, Method and application to human serum proteins. *Ann. New York Acad. Sci.*, 1964, 121: 404-427). In general, a solution containing acrylamide monomer and bisacrylamide as the crosslinking reagent is polymerized in appropriate buffers in the presence of an initiator at room temperature. The desired resolution of the gels can be achieved by adjustment of the concentrations of the various components of the gel solution. The components and concentrations thereof for producing gel solutions of different supporting matrices for various applications are well known to one skilled in the art.

The basic apparatus used for gel electrophoresis includes (1) a gel cassette which holds the gel matrix between two plates and (2) an electrophoresis unit that holds the gel cassette and is connected to a power source which supplies the electric current that causes the molecules to move through the gel matrix. The electrophoresis unit also contains buffer chambers that place the top and bottom of the gel in contact with the buffer solution, which is an ionic solution that carries the electrical current through the gel matrix. Glass or plastic plates have typically been used to form the gel cassettes for casting polyacrylamide gels. Polyacrylamide gels held in glass cassettes show better resolution compared to those held in plastic cassettes upon performing gel electrophoresis. However, glass is fragile and not suitable for high throughput production due to the tedious procedures taken to prepare the gels. Plastic molds are now used more often to make precast gels because it is easier and more economical. Special surface coating of the plastic plates has been adapted to improve the resolution of the separated macromolecule bands.

A standard gel cassette is formed by binding the two glass or plastic plates together and temporarily sealing the bottom of the cassette with tape. Spacers are placed along the vertical side edges of each plate to create a space, or "gel chamber," between the plates for the gel matrix to fill. The gel matrix solution is poured into the sealed cassette and then solidified through polymerization. To form the sample holding compartments, known as "wells," a comb is inserted between the two plates at the top edge prior to completion of the gel polymerization process with the teeth of the comb extending downwardly into the gel matrix. In addition, the top edge of one plate is often cut away across the top length of the plate except at the vertical side edges to create a cutout that allows the buffer solution to access the top of the gel matrix once the cassette is placed in the electrophoresis unit. This cutout also facilitates sample loading into the wells.

The plate-to-plate distance defines the thickness of the gel. For example, a greater plate-to-plate distance will yield a thicker gel. In a standard gel cassette, the plate-to-plate distance is constant throughout the entire length and height of the plates. More specifically, for PAGE, the plate-to-plate distance of the standard gel cassette used in protein separation is 1 mm. Therefore, the thickness of the gel and the sample loading wells is also constant at 1 mm.

The sample volume that can be loaded onto the gel is limited by the size of the wells, and most can only accommodate small volumes. However, it is desirable to be able to load larger sample volumes on gels, especially for the analysis of target molecules with low concentrations in the sample. To increase the size of the wells, and therefore the amount of sample that can be loaded, there are two approaches that are routinely employed. The first approach is to produce thicker gels. This increases the volume of the wells proportionally to the thickness of the gel. However, thicker gels require a greater current for a given field strength during electrophoresis. Use of a greater current can lead to greater heat build up in the gels, which in turn decreases gel resolution and performance. Thicker gels may also lead to less efficient protein transfer, which is necessary for common downstream analyses such as Western blotting. The second solution for increasing the sample volume that a well can accommodate is to increase the depth of the wells by using combs with longer teeth. However, the increased sample height in the wells after loading reduces the gel resolution and can sometimes lead to inefficient separation between proteins or other biological molecules of similar size.

Gel resolution and performance are also affected by other factors in addition to those discussed above. For the best resolution, it is desirable to load the sample as close to the bottom of the well as possible. As a practical matter, it is difficult to load samples into the wells of the standard 1 mm gel cassette used in PAGE, because the space between the plates is too narrow to allow a standard pipette tip to fit between the plates and reach the bottom of wells. Furthermore, the sample runs through the gel in the sample lane as it is loaded onto the gel and sits in the well. However, once the comb is removed after polymerization, the walls of the sample wells are not held in place and are free to move. This can lead to skewed sample lanes, difficulty in sample loading, and distorted macromolecule bands after electrophoresis.

BRIEF SUMMARY OF THE INVENTION

Therefore, a need exists for a gel cassette that is capable of holding an increased sample volume without changing the thickness of the gel and the height of the wells, such that larger sample volumes can be loaded without compromising the resolution of the gel, and without the need to change the electrophoresis unit in which the gel cassette is held. Furthermore, it is desirable to design the gel cassette such that the walls of the sample wells are held in place after the comb is removed to facilitate sample loading and further improve gel resolution.

The present invention provides an improved device for making a precast gel for performing gel electrophoresis, particularly for PAGE. The device is comprised of a gel cassette, a comb, and a gel matrix that when assembled together form sample wells that can hold an increased sample volume as compared to that of the wells formed in a gel using a standard gel cassette and comb. According to embodiments of the present invention, a larger sample volume can be loaded in the wells of the gel with improved gel resolution upon electrophoresis, as compared to other methods known in the art for increasing the volume of the sample wells.

One aspect of the present invention provides a gel cassette comprising a front plate and a back plate, wherein at least one plate has an inner surface with a stepped configuration. The plate with a stepped configuration has a top portion and a bottom portion, such that the top portion of the plate is at least 0.05 mm thinner than the bottom portion. Thus, when the inner surfaces of the front and back plates are placed face-to-face and fastened together, the space created between the two plates, defining the gel chamber, is larger at the top portion of the gel cassette than at the bottom portion.

Another aspect of the present invention provides a comb inserted in the top opening of the gel cassette, the comb having at least one tooth that extends downwardly into the gel matrix. The thickness of the tooth or teeth of the comb is substantially equal to the spacing formed between the top portions of the front and back plates. In a preferred embodiment, the length of the teeth of the comb is substantially equal to the height of the thinner top portion of the plate(s). According to embodiments of the present invention, when the comb is inserted into the gel cassette, thicker wells having an increased volume are formed, as compared to the volume of wells formed using the standard gel cassette and comb where the plate-to-plate distance and thickness of the wells is constant throughout.

Another aspect of the present invention provides a gel cassette wherein the back plate contains a groove configured in its top portion to create a network between the walls of the sample wells in the polymerized gel matrix. The groove is at least 0.05 mm wide and 0.05 mm deep. After the comb is inserted in the cassette, the gel matrix fills the gaps between the teeth of the comb and then flows into the groove. This provides a means for precisely positioning the sample well walls in place and prevents movement during sample loading and gel electrophoresis.

In a preferred embodiment of the present invention, the device for gel electrophoresis comprises a gel cassette having a front plate and a back plate wherein at least one plate has a stepped inner surface, such that the plate-to-plate distance at the bottom portion is 1 mm and the plate-to-plate distance at the top portion is at least 1.05 mm; and a comb wherein the thickness of the teeth is greater than 1 mm and is substantially equal to the plate-to-plate distance at the top portion of the gel cassette. The volume of the sample wells in a gel casted using the device as described in this preferred embodiment is at least 10% larger than that of the sample wells of a 1 mm thick gel casted using a standard 1 mm gel cassette and comb.

BRIEF DESCRIPTION OF THE SEVERAL VIEWS OF THE DRAWINGS

In order for the aspects of the present invention to be more clearly understood, various embodiments will be further described in the following detailed description of the invention with reference to the accompanying drawings, where corresponding reference numerals refer to corresponding components. The drawings and following detailed description are intended to provide examples of various embodiments of the present invention. It should be understood that the scope of the invention is not limited by the drawings and discussion of these specific embodiments.

In the drawings.

DETAILED DESCRIPTION OF THE INVENTION

All publications and patents referred to herein are incorporated by reference. Unless defined otherwise, all technical and scientific terms used herein have the same meaning as commonly understood to one of ordinary skill in the art to which this invention pertains. Otherwise, certain terms used herein have the meanings as set forth in the specification.

As used herein, the term "gel cassette" refers to the device assembled from two plates aligned face-to-face and fastened together with a spacing formed between the two plates. The spacing formed between the two plates is referred to as the "gel chamber." The gel matrix is held within the gel chamber. Certain terms describing the dimensions and other aspects of the gel cassette have the following meanings: "top length" of a plate refers to the dimension extending in a direction perpendicular to the vertical side edges of the plate along its top edge; "plate-to-plate distance" refers to the distance measured between the two plates extending in a direction perpendicular to the faces of the plates; "top opening" or "spacing at the top portion" refers to the space between the two plates accessible near the top edges of the plates; "bottom opening" or "spacing at the bottom portion" refers to the space between the two plates accessible near the bottom edges of the plates; and "gel thickness" refers to the dimension of the gel in a direction perpendicular to the faces of the plates assembled to form the gel cassette.

As used herein the terms "well" or "sample well" refer to the sample compartments formed in the gel matrix along the top edge of the gel cassette by the teeth of the comb when the comb is inserted into the top opening of the gel cassette with the teeth extending downwardly into the gel matrix. "Well thickness" refers to the dimension of the well in a direction perpendicular to the faces of the gel cassette plates.

As used herein, the terms and phrases "standard gel cassette" and "standard gel cassette and comb" all refer to a device for gel electrophoresis in which the plate-to-plate distance between the plates of the gel cassette is constant throughout. More specifically, the terms "standard 1 mm gel cassette" and "standard 1 mm gel cassette and comb" refer to a device for gel electrophoresis in which the plate-to-plate distance between the plates of the gel cassette, gel thickness and well thickness are constant throughout at 1 mm. The thickness of the teeth of a comb used with a standard 1 mm gel cassette is understood to be 1 mm.

Figure 1A:
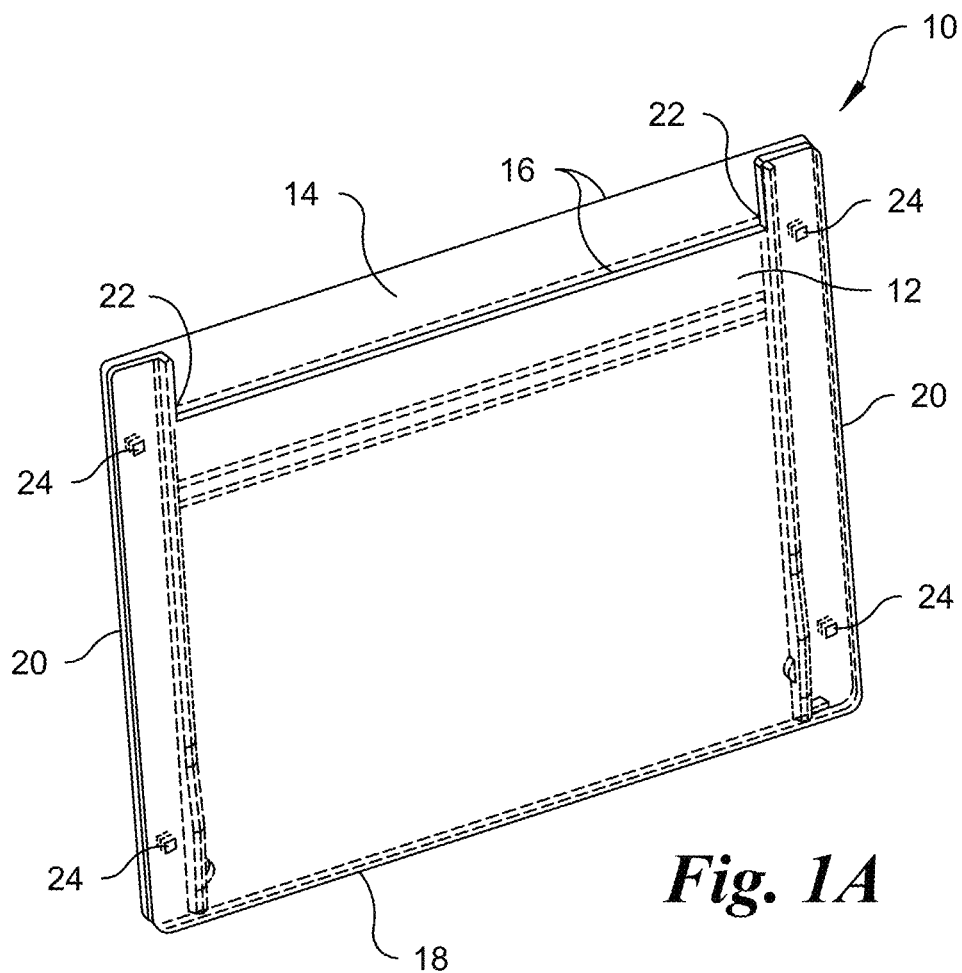
FIGS. 1A & 1B are respectively a side perspective view and a cross-sectional view of an assembled gel cassette comprising two plastic plates according to an embodiment of the present invention.

Referring in detail to the drawings, FIG. 1A depicts a gel cassette generally indicated by the reference numeral 10 that is assembled according to embodiments of the present invention. Gel cassette 10 is comprised of two plates, a front plate 12 and a back plate 14, with the front plate and back plate each having a top edge 16, a bottom edge 18, and two side edges 20. Each plate has two surfaces, an inner surface and outer surface. The inner surfaces of the front and black plates are oriented face-to-face with their respective edges aligned during assembly of the gel cassette. The inner faces of the front plate and back plate are depicted in greater detail in FIGS. 2A and 3A respectively, as discussed below. The top edge 16 of the front plate contains a cutout 22 across its top length except at the two side edges to allow access of the top edge of the gel matrix to the buffer solution during electrophoresis and to facilitate sample loading. Thus, the top edge of the front plate can be lower than the top edge of the back plate in the assembled gel cassette.

The two plates of the gel cassette may be assembled together via any suitable method such as ultrasonic welding. After assembly, the bottom opening of the cassette may or may not be sealed by any suitable tape, sealant, or polymeric materials. The gel solution poured into the gel cassette may be any suitable matrix material, including but not limited to polyacrylamide, agarose, and starch, but is most preferably polyacrylamide. The plates may be made of any suitable materials, preferably plastics including but not limited to polyethylene terephthalate, polyvinyl chloride, polymethyl mathacrylate, acrylonitrile-styrene, polystyrene, polyethylene, or various copolymers. The plates may also be transparent to facilitate the viewing of the electrophoresis process.

Figure 1B:
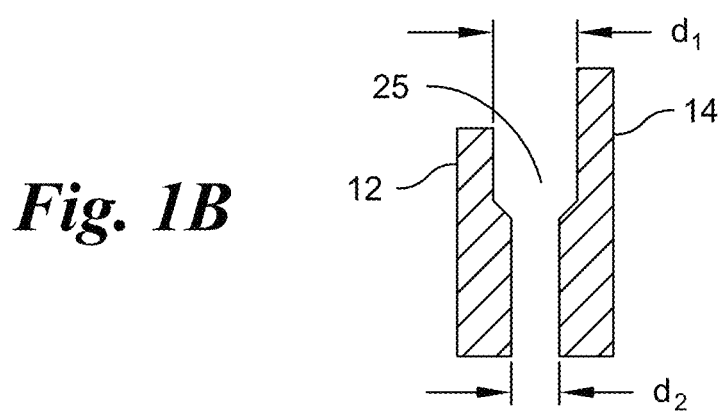

According to embodiments of the present invention, the front and back plates of the gel cassette have additional features such as bumps and posts 24 (FIG. 1) at the side edges of the plates to facilitate assembly. These additional features along the side edges of the plates also function as the spacers to space the plates apart and create a gel chamber 25 in which the gel matrix is held (FIG. 1B). Specifically, the bumps function as spacers during the process of assembling the gel cassette, and the posts hold the two plates together and also avoid the deformation of the plates during the assembly process. These additional features may be made of any suitable plastic materials, including but not limited to polyethylene terephthalate, polyvinyl chloride, polymethyl mathacrylate, acrylonitrile-styrene, polystyrene, polyethylene, or various copolymers, and preferably are made of the same material as the plates.

Figure 2A:
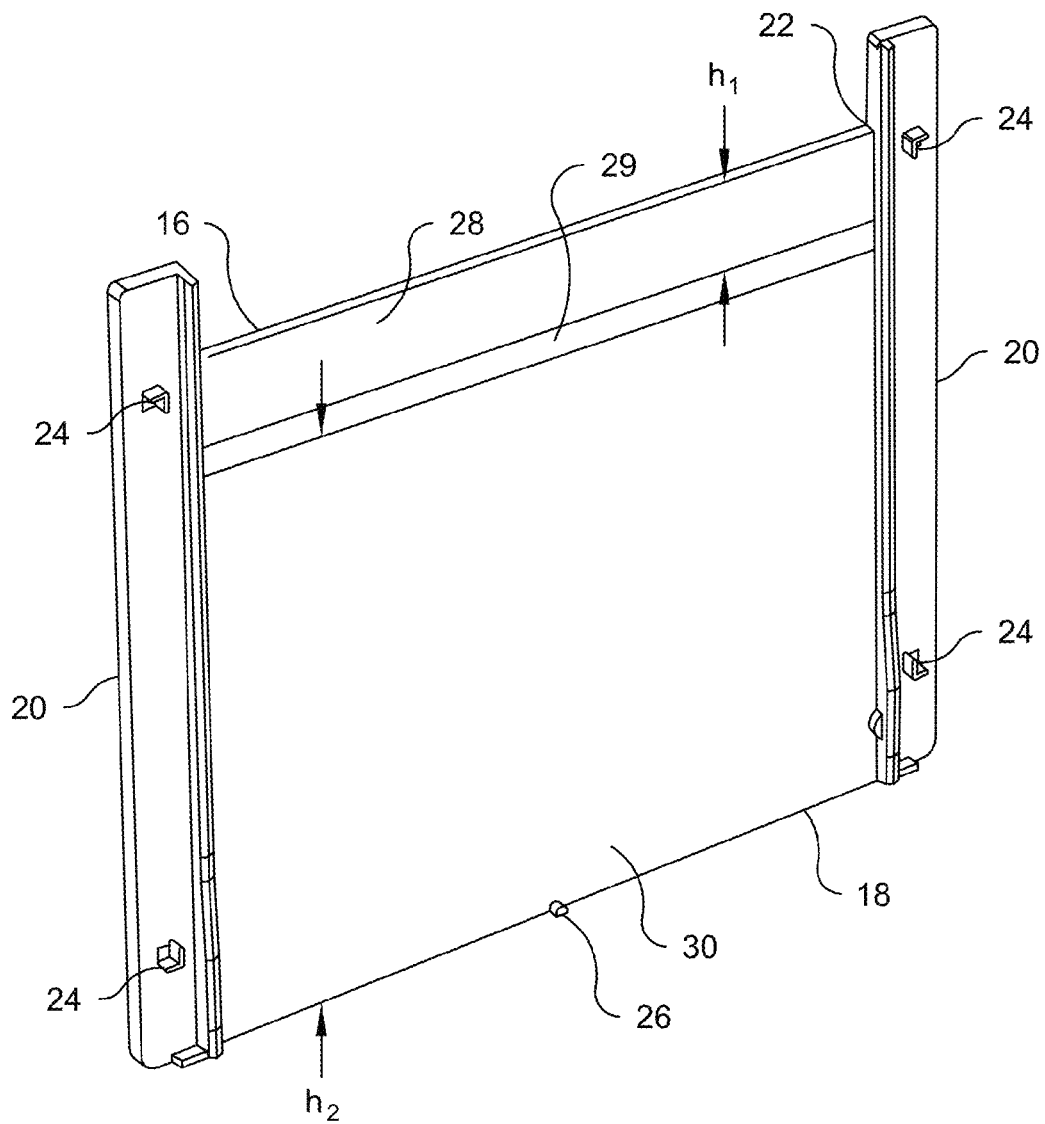
FIGS. 2A & 2B are respectively a side perspective view of the inner surface and a cross-sectional thickness view of a front plate according to an embodiment of the present invention.
Figure 3A:
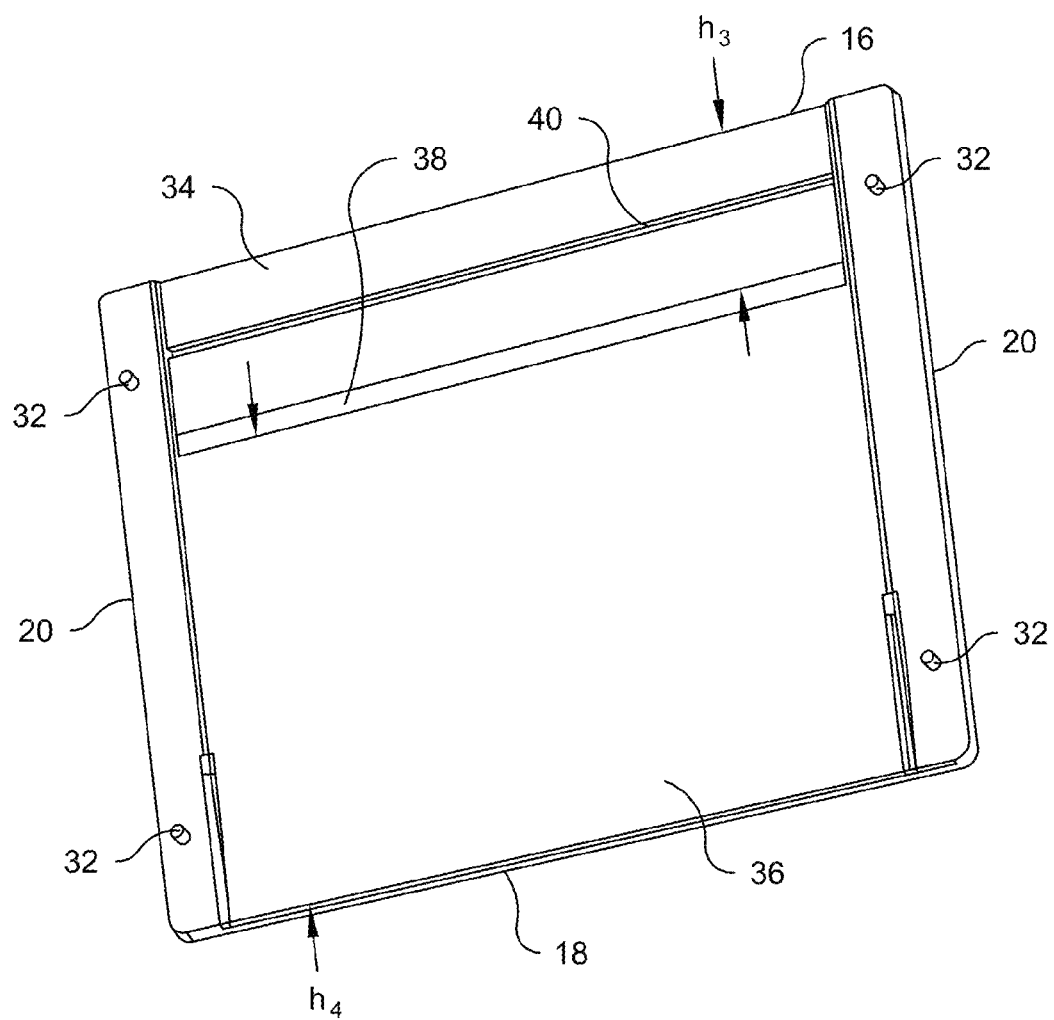
FIGS. 3A & 3B are respectively a side perspective view of the inner surface and a cross-sectional thickness view of a back plate according to an embodiment of the present invention.

FIGS. 2A and 3A, which are respectively a side perspective view of the inner surface of a front plate and a side perspective view of the inner surface of a back plate, depict additional features to facilitate assembly of the two plates together according to embodiments of the present invention. A cylinder-shaped post 26 at the bottom of the front plate is configured to prevent the incurvation of the back plate during the assembly process. The corner-shaped posts 24 located on the side edges of the front plate assist in the precise assembly of the front and back plates together to form the gel cassette. As shown in FIG. 3A, the back plate has four cylinder-shaped posts 32 located at its side edges. The cylinder-shaped posts 32 are configured to fit into the corner-shaped posts 24 on the side edges of the front plate during assembly of the gel cassette to precisely position the plates together. Any additional features for positioning and fastening the front and back plates together, such that they are spaced apart to create a gel chamber, may be used and are not limited to those specifically described here.

Figure 2B:
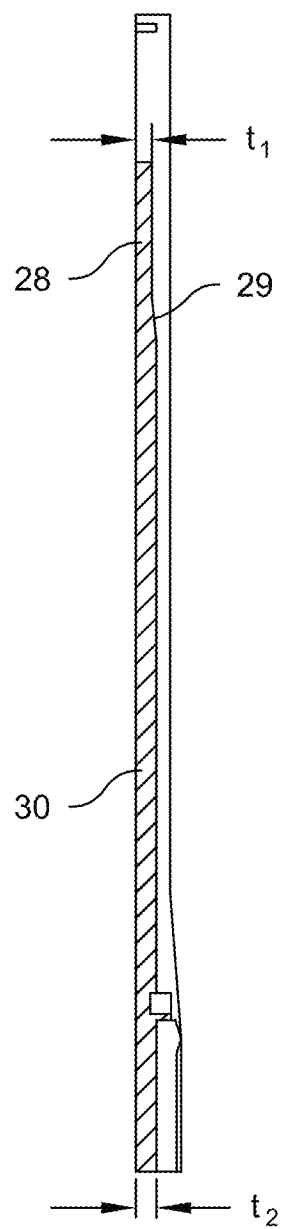

According to embodiments of the present invention, the inner surface of at least one plate of the gel cassette has a stepped configuration, such that the plate has a top portion and a bottom portion, wherein the top portion of the plate is thinner than the bottom portion of the plate. As shown in FIGS. 2A and 2B, the latter of which depicts a cross-sectional thickness view of the front plate with a stepped configuration according to embodiments of the invention, the inner surface of the front plate has a top portion 28 and a bottom portion 30. The top portion 28 and bottom portion 30 are separated by a stepped region 29. The top portion has a height, $h_1$, that is measured from the stepped region to the top edge 16, and the bottom portion has a height $h_2$ that is measured from the stepped region to the bottom edge 18 of the plate. Preferably, $h_1$ is smaller than $h_2$. In a preferred embodiment, the height of the top portion $h_1$ is at least the same as the length of the teeth of the comb used to form the sample wells. Specific embodiments of the comb according to the present invention are discussed in more detail below.

Referring to the cross-sectional thickness view of the front plate in FIG. 2B, the top portion has a thickness $t_1$ and the bottom portion has a thickness $t_2$. According to embodiments of the invention, $t_1$ is at least 0.05 mm thinner than $t_2$. For example, $t_1$ can be 1.4 mm and $t_2$ can be 1.8 mm. In other embodiments, $t_1$ and $t_2$ can be equal, provided that the back plate has an inner surface with a stepped configuration, as discussed in more detail below.

Figure 3B:
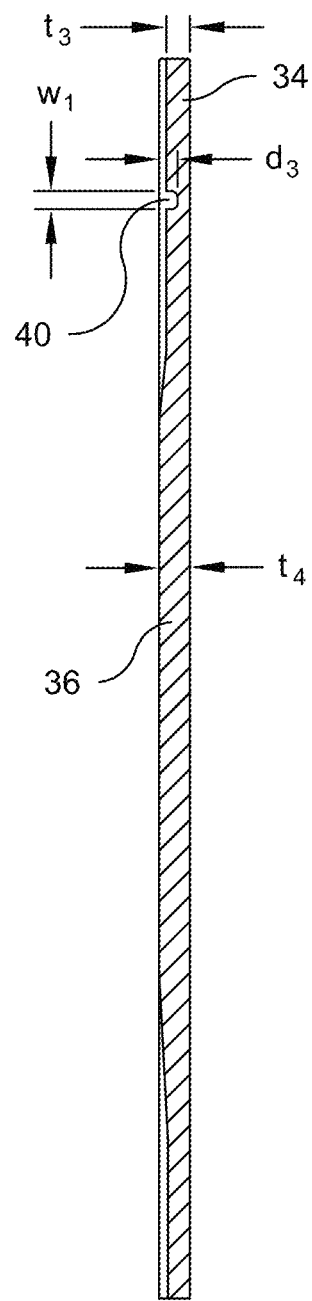

In another embodiment of the present invention, the back plate has an inner surface with a stepped configuration as shown in FIGS. 3A and 3B. Referring to the side perspective view of the inner surface of the back plate in FIG. 3A, the back plate has a top portion 34 and a bottom portion 36 separated by a stepped region 38. The top portion has a height $h_3$ that is measured from the stepped region 38 to the top edge 16 of the back plate, and the bottom portion has a height $h_4$ that is measured from the stepped region to the bottom edge 18 of the back plate. Preferably, $h_3$ is smaller than $h_4$. In a preferred embodiment, the height of the top portion $h_3$ is at least the same as the length of the teeth of the comb used to form the sample wells. Specific embodiments of the comb according to the present invention are discussed in more detail below.

Referring to the cross-sectional thickness view of the back plate shown in FIG. 3B, the top portion 34 has a thickness $t_3$ and the bottom portion 36 has a thickness $t_4$. According to embodiments of the invention, $t_3$ is at least 0.05 mm thinner than $t_4$. According to another embodiment, $t_3$ and $t_4$ can be equal provided that the front plate has a stepped configuration wherein $t_1$ is at least 0.05 mm thinner than $t_2$ as discussed above and shown in FIG. 2B.

According to embodiments of the present invention, the plate-to-plate distance $d_1$ at the top opening of the gel cassette (FIG. 1B) is greater than the plate-to-plate distance $d_2$ at the bottom opening of the gel cassette because at least one plate of the gel cassette has an inner surface with a stepped configuration. In one embodiment (as shown, for example, in FIG. 1B), both the front and back plates have a stepped configuration, such that the top portions of the plates are thinner than the bottom portions. In other words, $t_1$ is at least 0.05 mm thinner than $t_2$ (FIG. 2B) and $t_3$ is at least 0.05 mm thinner than $t_4$ (FIG. 3B). In another embodiment, only the front plate has a stepped configuration such that the top portion of the front plate is thinner than its bottom portion, and the top and bottom portions of the back plate are of equal thickness. In other words, $t_1$ is at least 0.05 mm thinner than $t_2$, and $t_3$ is equal to $t_4$. In yet another embodiment, only the back plate has a stepped configuration such that the top portion of the back plate is thinner than its bottom portion, and the top and bottom portions of the front plate are of equal thickness. In other words, $t_1$ is equal to $t_2$, and $t_3$ is at least 0.05 mm thinner than $t_4$.

According to another embodiment of the invention, the plate-to-plate distance $d_1$, also referred to as the spacing at the top portion of the plates, is constant throughout the top portion of the gel cassette. In addition, the plate-to-plate distance $d_2$, also referred to as the spacing at the bottom portion of the plates, is constant throughout the bottom portion of the gel cassette.

Another aspect of the present invention provides a comb that is inserted in the spacing at the top opening of the gel cassette. As used herein, the term "comb" refers to the template used to create the sample wells. The comb is comprised of a rectangular support structure, hereinafter referred to as the "spine," and finger-like protrusions that extend downward from the spine along its length, referred to as "a tooth" or "teeth." Each tooth has two faces, a front face and a back face. The spine also has a two faces, a front face and a back face. Certain terms used herein describing the dimensions of the teeth have the following meanings: "length" refers to the dimension in a direction extending from the interface where the tooth meets the spine of the comb to the extreme tip of the tooth; "thickness" refers to the dimension in a direction extending from the front face of the tooth to the back face of the tooth; and "width" refers to the dimension in a direction extending across the face of the tooth perpendicular to its length. The comb may be made of any suitable materials, preferably plastics including but not limited to polyethylene terephthalate, polyvinyl chloride, polymethyl mathacrylate, acrylonitrile-styrene, polystyrene, polyethylene, or various copolymers.

Figure 4:
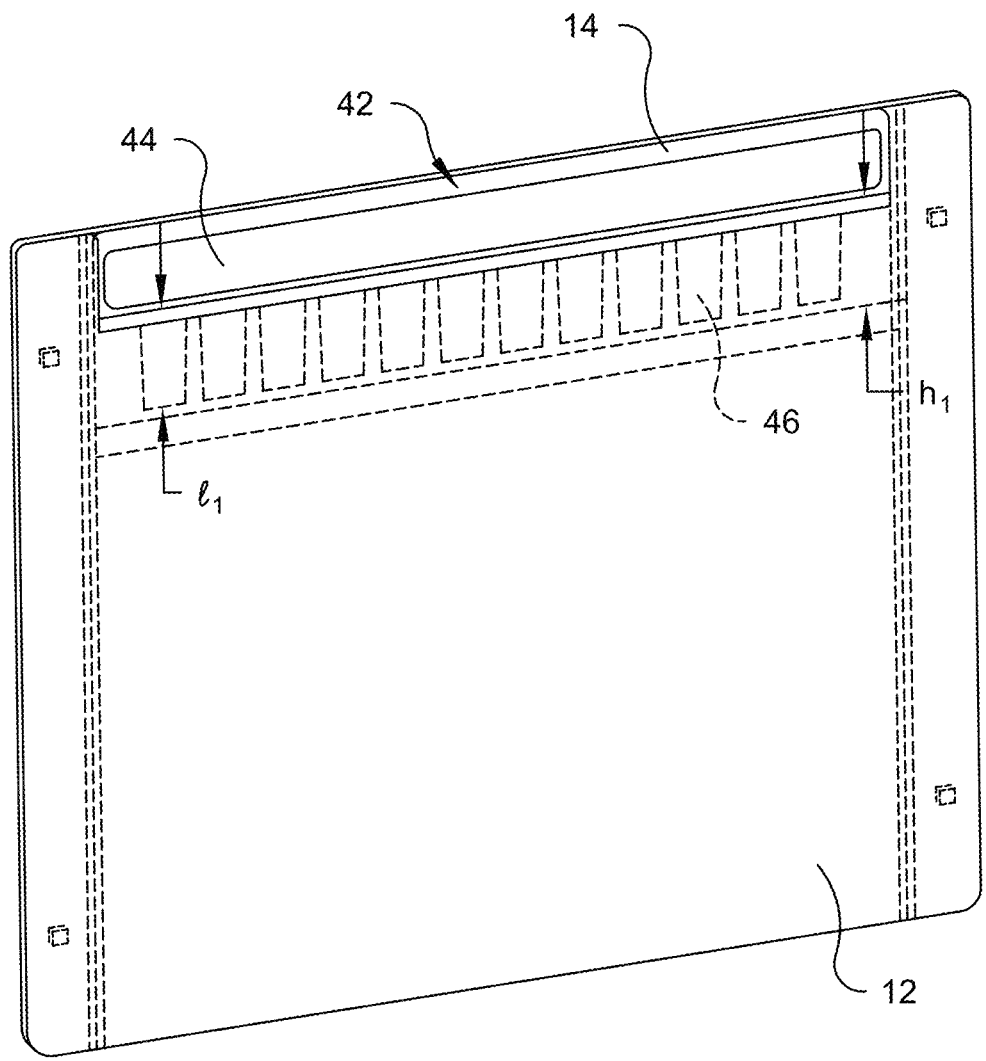
FIG. 4 shows an assembled apparatus comprising a gel cassette and a twelve-toothed comb according to an embodiment of the present invention.

FIG. 4 shows an example of a gel cassette with a comb 42 inserted into the top opening of the gel cassette according to embodiments of the present invention. The comb is comprised of a spine 44 and at least one tooth 46. In the specific example shown in FIG. 4, the comb has twelve teeth. According to embodiments of the invention, the comb has at least one tooth and can have fifteen teeth or more.

Figure 5A:
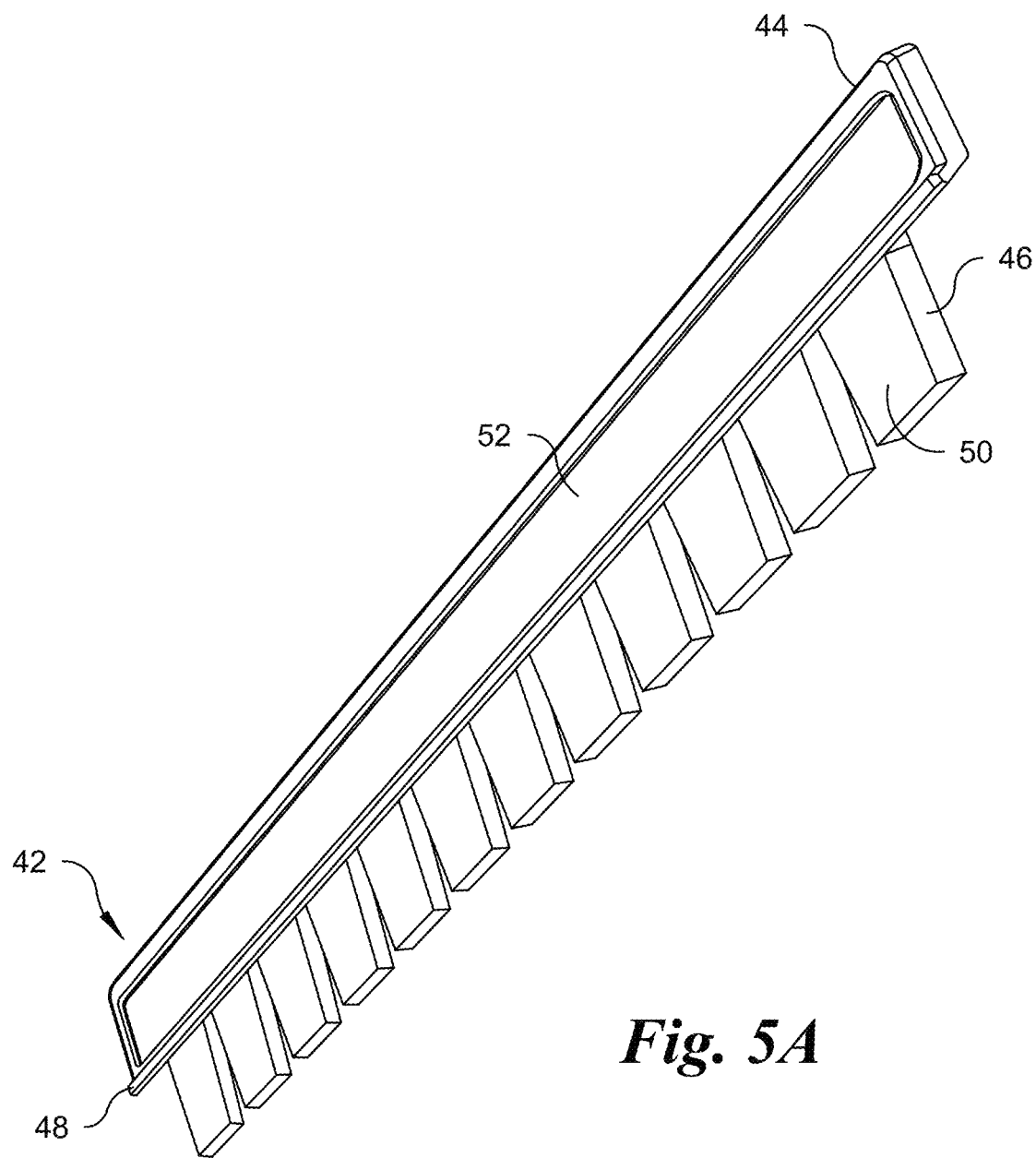
FIGS. 5A-5D are respectively a perspective front side view, a perspective back side view, a back side plan view, and a cross-sectional view of a twelve-toothed comb according to various embodiments of the present invention.
Figure 5B:
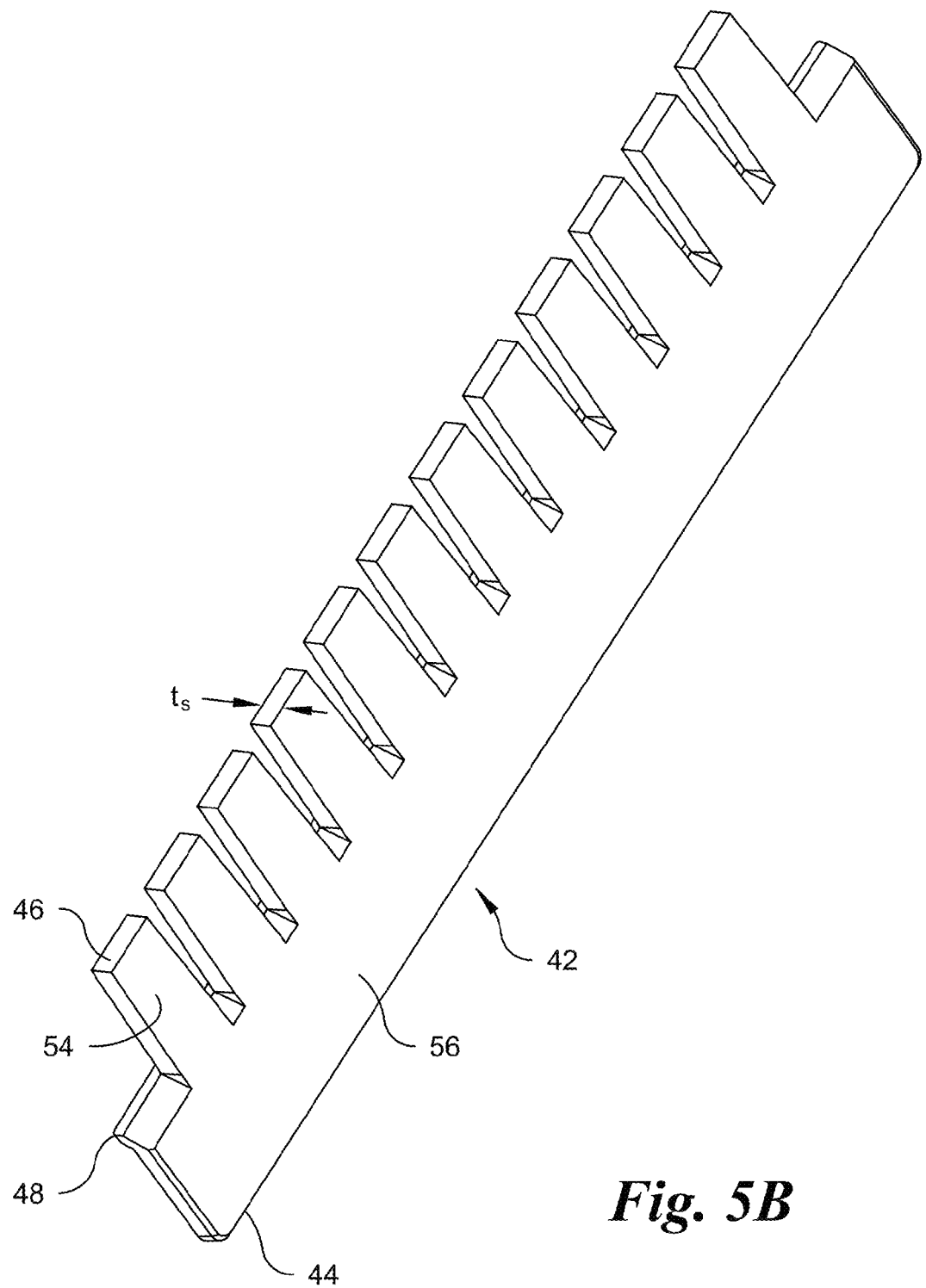
Figure 5C:
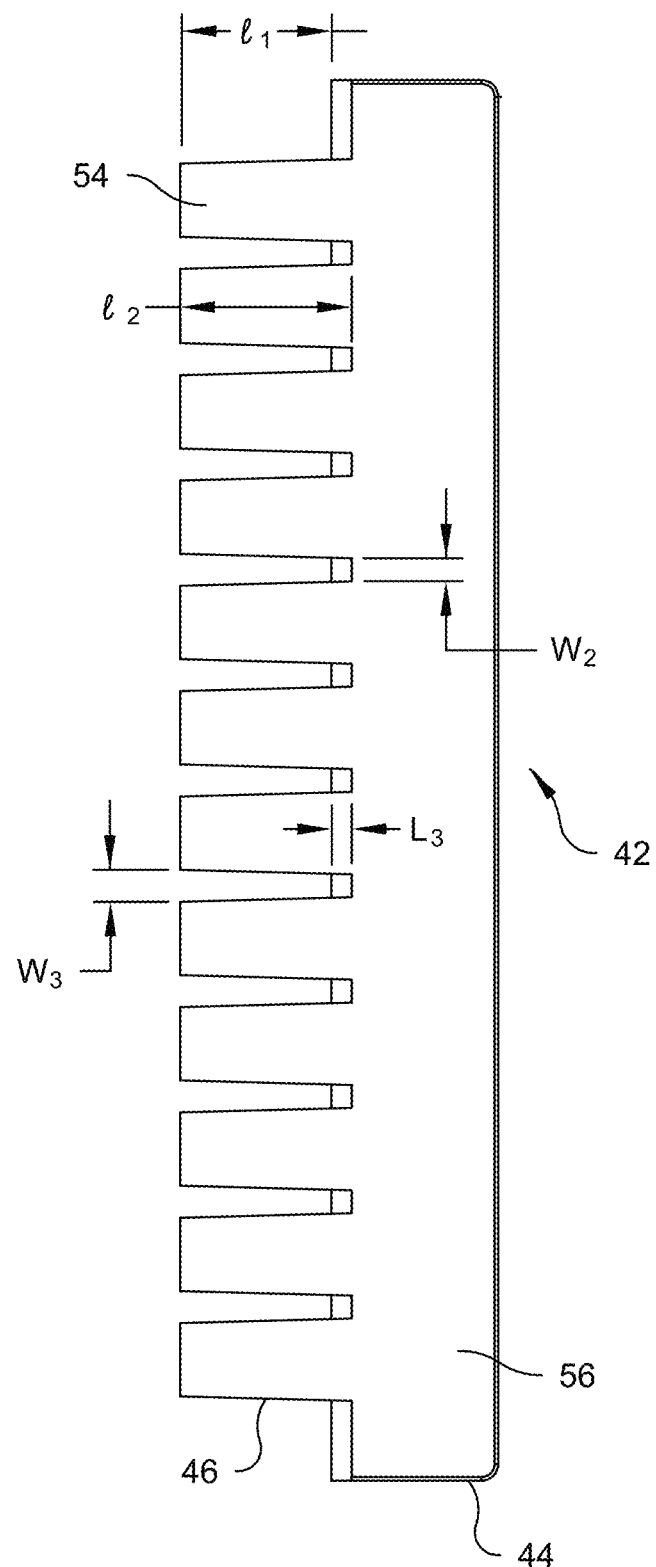

FIGS. 5A-5D respectively show a perspective front side view, a perspective back side view, a back side plan view, and a cross-sectional thickness view of a twelve-toothed comb according to embodiments of the present invention. Preferably, as shown in FIG. 5C, the teeth are spaced evenly apart along the length of the spine of the comb. More preferably, each tooth has a width that is greater proximal to the spine of the comb and tapers slightly inward distal to the spine of the comb creating a trapezoidal shape. Thus, the width $w_2$ between the space of any two teeth proximal to the spine is less than the width $w_3$ of the space between any two teeth distal to the spine. For example, $w_2$ can be 1.4 mm and $w_3$ can be 2.03 mm.

According to embodiments of the present invention, the teeth of the comb have a thickness $t_5$ (FIGS. 5B and 5D), that is substantially equal to the plate-to-plate distance $d_1$ (FIG. 1) at the top portion of the plates of the assembled gel cassette. Thus, when the comb is inserted into the spacing at the top opening of the gel cassette, the front face 50 of each tooth is flush against the inner surface of the top portion of the front plate, and the back face 54 of each tooth is flush against the top portion of the inner surface of the back plate.

Figure 5D:
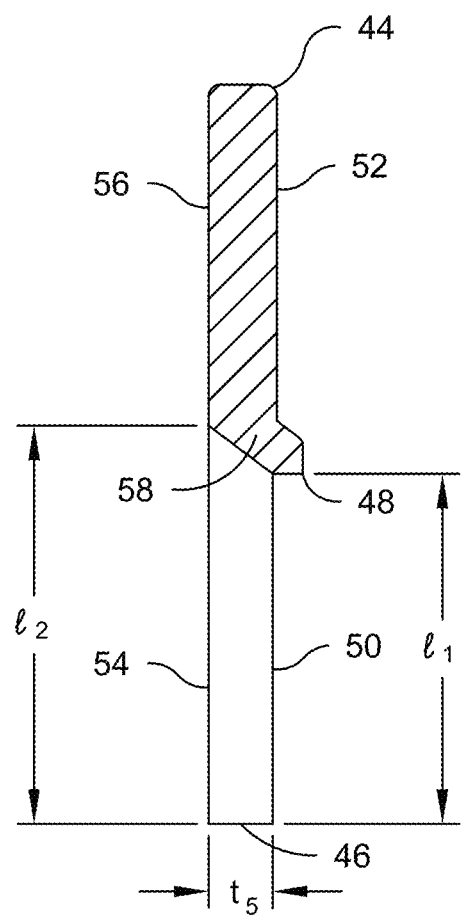

Another aspect of the present invention provides that the comb has a flange 48 (FIG. 5A). The flange is configured along the length of the spine 44 of the comb on its front face 52 at the interface whereat the spine meets the teeth. Referring to FIG. 5D, the flange extends outward in a direction substantially perpendicular to the front face 50 of each tooth. When the comb is inserted into the spacing at the top opening of the gel cassette with the front faces 50 of the teeth aligned face-to-face with the inner surface of the front plate, the flange rests on the top edge of the front plate. As shown in the back side view of the twelve-toothed comb in FIG. 5B, the flange is only present on the front face of the spine, such that the back face 54 of each tooth is flush with the back face 56 of the spine.

According to another embodiment of the present invention, a groove 40 is configured in the top portion of the inner surface of the back plate of the gel cassette as shown in FIGS. 3A and 3B. The groove 40 extends across the top length of the plate except at the two side edges in a direction parallel to the top edge of the plate. The groove is preferably positioned in the top portion of the back plate, such that when the front and back plates are assembled together to form the gel cassette, the groove sits below the top edge of the front plate, but above the stepped region of the front plate. Referring to FIG. 3B, the groove has a depth $d_3$ that is at least 0.05 mm, and a width $w_1$ that is at least 0.05 mm. For example, $d_3$ can be 0.8 mm and $w_1$ can be 1.2 mm. The depth $d_3$ of the groove is less than the thickness of the top portion $t_3$ of the back plate. The purpose of the groove is to allow for the formation of a gel network between the walls of the sample wells after polymerization of the gel matrix within the gel chamber. This gel network functions to precisely hold the sample wells in position to facilitate sample loading and improve gel resolution.

According to yet another embodiment of the present invention, the length of the front face of each tooth of the comb is less than the length of the back face of each tooth. Referring to FIGS. 5C and 5D, the length of the front face of each tooth is at least 0.05 mm less than the length of the back face $l_2$ of each tooth. The difference in length between the two faces of each tooth is represented by $l_3$ (FIG. 5C). The canted cut of the teeth at the interface where the teeth meet the spine, creating a bevel 58 (FIG. 5D), allows for the gaps between the teeth to be connected by the groove 40 on the back plate (FIGS. 3A and 3B). After the comb is inserted into the gel cassette, the gel matrix in the cassette fills in the gaps between the teeth first, and then flows into the groove on the back plate.

In a preferred embodiment of the present invention, the gel cassette has a plate-to-plate distance $d_2$ at the bottom opening equal to 1 mm, and a plate-to-plate distance $d_1$ at the top opening that is at least 1.05 mm; and the thickness of the teeth of the comb $t_5$ is substantially equal to $d_1$ and is therefore greater than the thickness of the teeth of a comb used with a standard 1 mm gel cassette. Compared to the standard 1 mm gel cassette, in which the plate-to-plate distance throughout the entire gel cassette is 1 mm and the thickness of the wells is 1 mm, the sample volume in a gel cassette assembled according to this preferred embodiment of the present invention can be increased by about 10% to 120%.

Figures 6A, 6B:
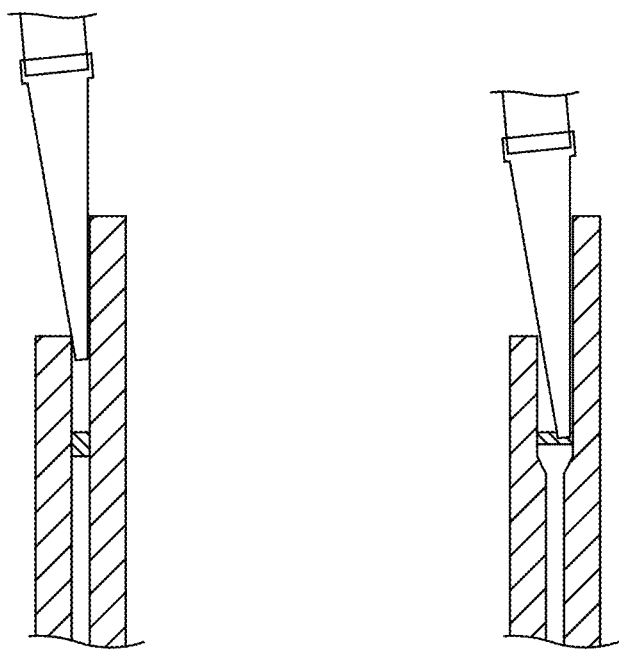
FIGS. 6A & 6B are cross-sectional views illustrating respectively the differences in sample loading between a standard 1 mm gel cassette and a 1 mm gel cassette assembled according to an embodiment of the present invention.

A related aspect of this preferred embodiment of the present invention provides that the plate-to-plate distance at the top portion of the gel cassette is large enough such that a standard pipette tip can reach the bottom of the sample wells during sample loading without damaging the gel. FIGS. 6A and 6B are respectively schematic representations of sample loading using a standard pipette tip with the standard 1 mm gel cassette, and sample loading using a standard pipette tip with a gel cassette assembled according to a preferred embodiment of the present invention. As shown in FIG. 6A, a standard pipette tip may not reach the bottom of the well in the standard 1 mm gel cassette. However, the top opening of the gel cassette assembled according to a preferred embodiment of the present invention is wide enough to allow for a standard pipette tip to fit through the top opening and reach the bottom of the well, such that the sample can be loaded directly into the bottom of the well (FIG. 6B). This feature will facilitate sample loading, simplify the experimental procedure, and improve gel resolution.

Figure 7A:
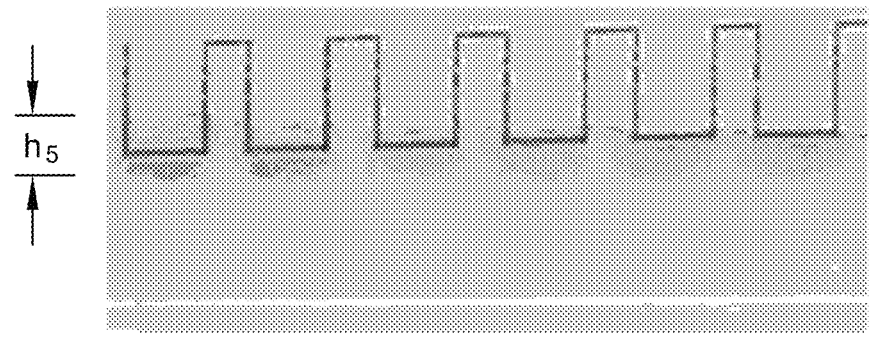
FIGS. 7A & 7B are respectively gel electrophoresis images using a standard 1 mm gel electrophoresis device and a 1 mm gel electrophoresis device assembled according to an embodiment of the present invention.
Figure 7B:
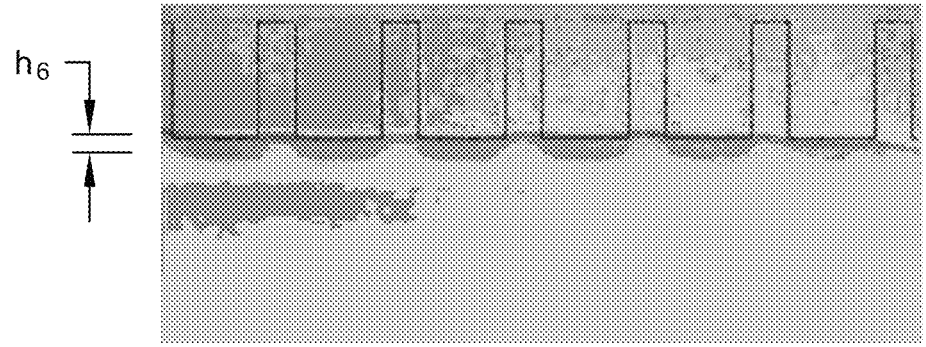

Another aspect of present invention provides that the sample height in the wells of the gel cassette is reduced after sample loading as compared to the sample height in the wells after loading the same volume in a standard gel cassette (see FIGS. 6A and 6B). In experiments conducted in support of the invention, gel electrophoresis using a standard 1 mm gel cassette was compared to gel electrophoresis using a gel cassette assembled according to a preferred embodiment of the present invention wherein the plate-to-plate distance at the bottom portion of the plates was 1 mm (FIGS. 7A and 7B). As shown in FIG. 7A, 6 µL of sample was loaded into each well of the standard 1 mm gel cassette and in FIG. 7B, 6 µL of sample was loaded into each well of a 1 mm gel cassette assembled according to an embodiment of the present invention. Pictures were taken after 2 min. of electrophoresis. The sample height $h_6$ observed using the presently invented gel cassette is 2-3 times shorter than the sample height $h_5$ in the standard 1 mm gel cassette. Thus, the wider top opening design of the gel cassette assembled according to embodiments of the present invention leads to a reduced sample height as compared to that in a standard gel cassette, which ultimately improves gel resolution.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for performing gel electrophoresis, the device comprising:
   (i) a gel cassette comprising a front plate and a back plate, the front plate and the back plate each having an inner surface, a top edge, a bottom edge and two side edges, the front and back plates being fastened together along at least the two side edges, such that the inner surfaces are face-to-face with a spacing there between forming a gel chamber, wherein the inner surface of at least one of the front and back plates has a stepped configuration such that the at least one plate has a top portion and a bottom portion, wherein the top portion has a thickness at least 0.05 mm thinner than the bottom portion, and the spacing forming part of the gel chamber between the plates is greater at the top portion than the spacing forming part of the gel chamber between the plates at the bottom portion;
   (ii) a gel matrix held within the gel chamber; and
   (iii) a comb inserted in the spacing at the top portion of the plates, the comb having a spine and at least one tooth extending from the spine downwardly into the gel matrix to form at least one well in the gel matrix, the at least one tooth having a thickness substantially equal to the spacing between the top portions of the plates, such that upon removal of the comb for performing the gel electrophoresis, the at least one well is bounded on opposite sides by the top portions of the plates.

2. The device according to claim 1, wherein the top portion of the at least one plate has a height, and the at least one tooth of the comb has a length, the height of the top portion of the at least one plate being at least substantially equal to the length of the at least one tooth of the comb.

3. The device according to claim 1, wherein the front plate of the gel cassette contains a cutout, the cutout extending across a top length of the front plate except at the two side edges, such that the front plate has a lower top edge than the top edge of the back plate.

4. The device according to claim 1, wherein the back plate of the gel cassette has a groove, the groove configured in the inner surface of the back plate along its top portion, the groove extending in a direction parallel to its top edge between the two side edges, the groove positioned between the top edge and bottom portion of the front plate when the front and plates are fastened together, wherein the groove contains gel matrix to provide a gel network connecting the walls of adjacent wells.

5. The device according to claim 4, wherein the groove has a width that is at least 0.05 mm and a depth that is at least 0.05 mm.

6. The device according to claim 1, wherein the at least one tooth of the comb has a front face and a back face, the at least one tooth cut from the support at an angle creating a bevel, such that the front face of the at least one tooth is shorter than the back face of the at least one tooth.

7. The device according to claim 6, wherein the front face of the at least one tooth of the comb is at least 0.05 mm shorter than the back face of the at least one tooth of the comb.

8. The device according to claim 1, wherein the spine of the comb has a front face and a back face, wherein a flange is configured on the front face of the spine at an interface where the at least one tooth meets the spine, the flange extending outward in a direction substantially perpendicular to the front face of the at least one tooth of the comb, such that when the comb is inserted into the spacing at the top portion of the plates with the front face of the at least one tooth face-to-face with the inner surface of the front plate, the flange rests on the top edge of the front plate.

9. The device according to claim 1, wherein the comb has 1-15 teeth.

10. The device according to claim 1, wherein the spacing between the front and back plates of the gel cassette at the bottom portion is 1 mm.

11. The device according to claim 1, wherein both the front and back plates have an inner surface with a stepped configuration.

12. A device for performing gel electrophoresis, the device comprising:
(i) a gel cassette comprising a front plate and a back plate, the front plate and the back plate each having an inner surface, a top edge, a bottom edge and two side edges, the front and back plates being fastened together along at least the two side edges, such that the inner surfaces are face-to-face with a spacing there between forming a gel chamber, wherein the inner surface of at least one of the front and back plates has a stepped configuration such that the at least one plate has a top portion and a bottom portion, wherein the top portion has a thickness at least 0.05 mm thinner than the bottom portion, and the spacing forming part of the gel chamber between the plates is greater at the top portion than the spacing forming part of the gel chamber between the plates at the bottom portion; and
(ii) a comb inserted in the spacing at the top portion of the plates, the comb having a spine and at least one tooth extending from the spine downwardly into the gel chamber, the at least one tooth having a thickness substantially equal to the spacing between the top portions of the plates.

13. The device according to claim 12, further comprising a gel matrix held within the gel chamber, such that the at least one tooth of the comb extends into the gel matrix to form at least one well in the gel matrix, and upon removal of the comb for performing the gel electrophoresis, the wells are bounded on opposite sides by the top portions of the plates.

14. A method of performing gel electrophoresis, the method comprising:
(i) obtaining a device according to claim 1; and
(ii) applying a sample to the at least one well.

* * * * *